United States Patent
Toledano et al.

(10) Patent No.: US 11,071,878 B2
(45) Date of Patent: *Jul. 27, 2021

(54) CORE STABILIZED MICROCAPSULES, METHOD OF THEIR PREPARATION AND USES THEREOF

(71) Applicant: SOL-GEL TECHNOLOGIES LTD., Ness Ziona (IL)

(72) Inventors: Ofer Toledano, Kfar Saba (IL); Haim Bar-Simantov, Netanya (IL); Hanan Sertchook, Gedera (IL); Sharon Fireman-Shoresh, Tel Aviv (IL); Dorit Marco, Rehovat (IL)

(73) Assignee: Sol-Gel Technologies Ltd., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/924,331

(22) Filed: Mar. 19, 2018

(65) Prior Publication Data

US 2018/0207451 A1 Jul. 26, 2018

Related U.S. Application Data

(60) Continuation-in-part of application No. 15/834,805, filed on Dec. 7, 2017, which is a division of application No. 13/500,937, filed as application No. PCT/IL2010/001092 on Dec. 30, 2010, now Pat. No. 10,512,796.

(60) Provisional application No. 61/291,594, filed on Dec. 31, 2009.

(51) Int. Cl.

| | |
|---|---|
| *A61Q 19/00* | (2006.01) |
| *B01J 13/14* | (2006.01) |
| *A61K 9/51* | (2006.01) |
| *A61K 9/00* | (2006.01) |
| *A61K 8/67* | (2006.01) |
| *A61K 8/38* | (2006.01) |
| *A61K 8/26* | (2006.01) |
| *A61K 8/25* | (2006.01) |
| *A61K 8/11* | (2006.01) |
| *A61K 9/06* | (2006.01) |
| *A61K 9/50* | (2006.01) |
| *B01J 13/18* | (2006.01) |
| *F28D 20/02* | (2006.01) |
| *A61K 9/10* | (2006.01) |
| *A61K 47/38* | (2006.01) |
| *A61K 47/32* | (2006.01) |

(52) U.S. Cl.
CPC .......... *A61Q 19/00* (2013.01); *A61K 8/11* (2013.01); *A61K 8/25* (2013.01); *A61K 8/26* (2013.01); *A61K 8/38* (2013.01); *A61K 8/671* (2013.01); *A61K 9/0014* (2013.01); *A61K 9/06* (2013.01); *A61K 9/10* (2013.01); *A61K 9/501* (2013.01); *A61K 9/5115* (2013.01); *A61K 9/5192* (2013.01); *B01J 13/14* (2013.01); *B01J 13/18* (2013.01); *F28D 20/023* (2013.01); *A61K 9/5026* (2013.01); *A61K 47/32* (2013.01); *A61K 47/38* (2013.01); *A61K 2800/412* (2013.01)

(58) Field of Classification Search
CPC combination set(s) only.
See application file for complete search history.

(56) References Cited

U.S. PATENT DOCUMENTS

| | | | |
|---|---|---|---|
| 5,401,517 A * | 3/1995 | Meyers | A61K 8/671 424/401 |
| 5,468,471 A | 11/1995 | Zecchino et al. | |
| 5,500,223 A | 3/1996 | Behan et al. | |
| 5,720,949 A | 2/1998 | Davis | |
| 5,891,476 A | 4/1999 | Reo et al. | |
| 6,238,650 B1 | 5/2001 | Lapidot et al. | |
| 6,270,536 B1 | 8/2001 | Holman | |
| 6,303,149 B1 | 10/2001 | Magdassi et al. | |
| 6,337,089 B1 * | 1/2002 | Yoshioka | A61K 8/11 424/400 |
| 6,436,375 B1 | 8/2002 | Lapidot et al. | |
| 6,458,509 B1 | 10/2002 | Lapidot et al. | |
| 6,913,825 B2 | 7/2005 | Ostafin et al. | |
| 6,939,552 B2 | 9/2005 | Ansara et al. | |
| 6,979,440 B2 * | 12/2005 | Shefer | A61K 8/0204 424/78.02 |
| 8,617,580 B2 | 12/2013 | Toledano et al. | |
| 9,868,103 B2 | 1/2018 | Toledano et al. | |
| 2002/0064541 A1 | 5/2002 | Lapidot et al. | |
| 2003/0082217 A1 | 5/2003 | Afriat et al. | |
| 2004/0096419 A1 | 5/2004 | Golz-Berner et al. | |

(Continued)

FOREIGN PATENT DOCUMENTS

| | | |
|---|---|---|
| DE | 102004017221 A1 | 10/2005 |
| GB | 1450507 | 9/1976 |

(Continued)

OTHER PUBLICATIONS

"Aliphatic Compound" obtained online via www.wikipedia.com (2018).

(Continued)

*Primary Examiner* — Celeste A Roney

(74) *Attorney, Agent, or Firm* — Mark S. Cohen; Pearl Cohen; Zedek Latzer Baratz LLP

(57) ABSTRACT

The present invention provides core-stabilized microcapsules, wherein said core comprises at least one active agent encapsulated within an inorganic oxide shell, processes for their preparations, comparisons comprising them and uses thereof.

9 Claims, No Drawings

(56) References Cited

U.S. PATENT DOCUMENTS

| | | | |
|---|---|---|---|
| 2007/0207113 A1* | 9/2007 | Joerger | A61K 8/345 424/70.31 |
| 2009/0226380 A1 | 9/2009 | Clark et al. | |
| 2010/0016443 A1 | 1/2010 | Toledano et al. | |
| 2010/0047357 A1 | 2/2010 | Toledano | |
| 2010/0255107 A1 | 10/2010 | Lapidot et al. | |
| 2011/0177951 A1 | 7/2011 | Toledano et al. | |
| 2012/0202695 A1 | 8/2012 | Toledano et al. | |
| 2013/0095185 A1 | 4/2013 | Toledano et al. | |
| 2018/0117369 A1 | 5/2018 | Toledano et al. | |
| 2018/0339176 A1 | 11/2018 | Toledano et al. | |

FOREIGN PATENT DOCUMENTS

| | | | | |
|---|---|---|---|---|
| JP | 2003534249 A | 11/2003 | | |
| WO | WO-2001080823 A2 | 1/2001 | | |
| WO | WO 01/80823 A1 * | 11/2001 | | |
| WO | WO/2003/034979 A2 | 5/2003 | | |
| WO | WO-03034979 A2 * | 5/2003 | | A61K 8/042 |
| WO | WO 2004/081222 A2 | 9/2004 | | |
| WO | WO 2005/009604 A1 * | 2/2005 | | |
| WO | WO-2005009604 A1 | 2/2005 | | |
| WO | WO 2004/097056 A1 | 10/2005 | | |
| WO | WO 2007/015243 A2 | 2/2007 | | |
| WO | WO 2008/072239 A2 | 6/2008 | | |
| WO | WO-2008093346 A2 * | 8/2008 | | A61K 9/0014 |
| WO | WO-2008093347 A2 | 8/2008 | | |
| WO | WO 2008/133482 A1 | 11/2008 | | |
| WO | WO 2008/134908 A1 | 11/2008 | | |
| WO | WO 2010/013250 A2 | 2/2010 | | |
| WO | WO 2011/080741 A2 | 7/2011 | | |
| WO | WO 2011080741 A2 | 7/2011 | | |

OTHER PUBLICATIONS

Bon et al. "Pickering stabilization as a tool in the fabrication of complex nanopatterned silica microcapsules" Langmuir. Sep. 11, 2007;23(19):9527-30.

Burkle GmbH, "Viscosity of Liquids", 2011.

Compilation under Creative Commons Attribution-Share Alike 3.0, "Viscosity", undated, pp. 1-20.

Flux, "Viscosity Chart", undated, p. 21.

Jenning et ai. "Comparison of wax and glyceride solid lipid nanoparticies (SLN®)" International journal of pharmaceutics. Mar. 10, 2000;196(2)219-22.

Jenning et al. "Encapsulation of retinoids in solid lipid nanoparticles (SLN)" Journal of microencapsulation. Jan. 1, 2001;18(2):149-58.

International Search Report for PCT Application No. PCT/IL2010/001092 dated Jul. 22, 2011.

Prestidge et al. "Nanoparticie encapsulation of emulsion droplets" International journal of pharmaceutics. Oct. 31, 2006;324(1):92-100.

Rowe et al. "Handbook of pharmaceutical excipients" Aug. 2009, pp. 155-156, 215-216, 247-249, 311-314; London, Pharmaceutical Press.

Smooth-On, "Viscosity Scales", undated.

"Symptoms and Causes of Vitiligo" Mayo Clinic: obtained online via www.mayoclinic.org on Jun. 4, 2018; pp. 1-3, 2018.

"Symptoms and Causes of Vitiligo" Mayo Clinic; obtained online via www.mayoclinic.org on Jun. 4, 2018; pp. 1-6, 2018.

"Treating Melanoma Skin Cance". obtained online via www.cancer.org on Jun. 4, 2018, pp. 1-7, 2016.

Date, A. A., Naik, B., & Nagarsenker, M. S. (2006). Novel drug delivery systems: potential in improving topical delivery of antiacne agents. Skin Pharmacology and Physiology, 19(1), 2-16.

Büchel, G., Grün, M., Unger, K. K., Matsumoto, A., & Kazuo, T. (1998). Tailored syntheses of nanostructured silicas: control of particle morphology, particle size and pore size. Supramolecular Science, 5(3-4), 253-259.

Del Rosso, J. Q., Pillai, R., & Moore, R. (2010). Absence of degradation of tretinoin when benzoyl peroxide is combined with an optimized formulation of tretinoin gel (0.05%). The Journal of Clinical and Aesthetic Dermatology, 3(10), 26.

He, J., Fujikawa, S., Kunitake, T., & Nakao, A. (2003). Preparation of porous and nonporous silica nanofilms from aqueous sodium silicate. Chemistry of materials, 15(17), 3308-3313.

Huo, Q., Feng, J., Schüth, F., & Stucky, G.D. (1997). Preparation of hard mesoporous silica spheres. Chemistry of Materials, 9(1), 14-17.

Nooney, R. I., Thirunavukkarasu, D., Chen, Y., Josephs, R., & Ostafin, A. E. (2002). Synthesis of nanoscale mesoporous silica spheres with controlled particle size. Chemistry of materials, 14(11), 4721-4728.

Nooney, R. I., Thirunavukkarasu, D., Chen, Y., Josephs, R., & Ostafin, A. E. (2003). Self-assembly of mesoporous nanoscale silica/gold composites. Langmuir, 19(18), 7628-7637.

Ozin, G. A. (1992). Nanochemistry: synthesis in diminishing dimensions. Advanced Materials, 4(10), 612-649.

Skapin, S. D., & Matijević, E. (2004). Preparation and coating of finely dispersed drugs: 4. Loratadine and danazol. Journal of colloid and interface science, 272(1), 90-98.

Tjandra, W., Yao, J., & Tam, K. C. (2006). Interaction between silicates and ionic surfactants in dilute solution. Langmuir, 22(4), 1493-1499.

* cited by examiner

CORE STABILIZED MICROCAPSULES, METHOD OF THEIR PREPARATION AND USES THEREOF

CROSS REFERENCE TO RELATED APPLICATIONS

This Application is a Continuation in Part Application of U.S. application Ser. No. 15/834,805 filed Dec. 7, 2017, which is a Divisional Application of U.S. application Ser. No. 13/500,937, filed on Apr. 9, 2012, now U.S. Pat. No. 10,512,796, granted Dec. 24, 2019, which is a National Phase Application of PCT International Application No. PCT/IL2010/001092, International Filing Date Dec. 30, 2010, claiming priority of United-States Provisional Application No. 61/291,594, filed Dec. 31, 2009, which are hereby all incorporated by reference.

FIELD OF THE INVENTION

This invention relates to microcapsules having stabilized core, method of their preparation and uses thereof.

BACKGROUND OF THE INVENTION

The following publications are considered pertinent for describing the state of the art in the field of the invention:
U.S. Pat. No. 5,500,223
U.S. Pat. No. 6,303,149
U.S. Pat. No. 6,238,650
U.S. Pat. No. 6,468,509
U.S. Pat. No. 6,436,375
U.S. Pat. No. 6,337,089
U.S. Pat. No. 5,891,476
DE 102004017221
WO 2008134908
U.S. Pat. No. 6,270,836
WO 2008/133482
WO 2005097056
S. A. F. Bon et al., Pickering Stabilization as a Tool in the Fabrication of Complex Nanopatterned Silica Microcapsules, *Langmir*, 23: 9527-9530, 2007.
C. A. Prestidge et al. Nanoparticle encapsulation of emulsion droplets, International Journal of Pharmaceutics 324: 92-100, 2006.
International Journal of Pharmaceutics, vol. 126 (2000) 219-222.
J. Volkhard et al. *J. Microencapsulation*, 18(2), 149-152, 2001.

SUMMARY OF THE INVENTION

The present invention provides a process for preparing microcapsules having a core encapsulated within an inorganic oxide shell, said process comprising:
(a) preparing an oil-in-water emulsion by emulsification of an oily phase comprising at least one active agent and at least one phase changing material in an aqueous phase, wherein at least one of said oily phase and aqueous phase comprise a sol-gel precursor;
(b) subjecting said emulsion to microcapsule forming conditions; thereby obtaining said microcapsules.
In one embodiment of the present invention, at least one inorganic oxide nanoparticle is added to said aqueous phase prior, during, or after emulsification of step (a).

In one embodiment, this invention provides a process for preparing microcapsules having a core encapsulated within an inorganic oxide shell, said process comprising:
(a) preparing an oil-in-water emulsion by emulsification of an oily phase, comprising at least one active agent and at least one phase changing material, in an aqueous phase, wherein at least one of said oily phase and aqueous phase comprise a sol-gel precursor;
(b) adjusting the pH of the emulsion to be in the range of 3 to 5; and
(c) subjecting said emulsion to microcapsule forming conditions; thereby obtaining said microcapsules;
wherein said core comprises at least one active agent and at least one phase changing material, which are both surrounded by an inorganic oxide shell.

The invention further provides microcapsules obtainable by the process of the invention.

In another one of its aspects, the invention provides microcapsules comprising a core encapsulated by an inorganic oxide shell, wherein said core has a viscosity of between about 300 cP to about 1,000,000 cP (when measured under various conditions, for example as will given herein below) and comprises at least one active agent and at least one phase changing material; wherein the thickness of said inorganic oxide shell is in the range of 0.02-10 micron, preferably in the range of 0.05-1 micron; and wherein said shell is obtained from a hydrolyzed and polymerized sol gel precursor. In one embodiment, said core comprises at least one active agent and at least one phase changing material. In other embodiments, said shell of said microcapsules of the invention is obtained from (a) inorganic oxide nanoparticles, and (b) a hydrolyzed and polymerized sol gel precursor.

The invention further encompasses a composition comprising microcapsules of the invention.

In a further aspect, the invention provides a method for treating a surface condition in a subject in need thereof, comprising topically administering to said subject a composition of the invention.

The invention further provides a composition comprising microcapsules of the invention, for the treatment of a disease, disorder or condition selected from acne, infection, inflammation, pruritus, psoriasis, seborrhea, contact dermatitis, rosacea, and a combination thereof.

In another aspect, the invention provides a use of microcapsules of the invention, for the preparation of a topically administered composition.

DETAILED DESCRIPTION OF THE INVENTION

The present invention is based on the finding of a process for obtaining a microcapsule having an inorganic oxide shell, wherein the incorporation of phase changing material into the core of said microcapsule provides unexpected stability to the encapsulated active agents in the core of said microcapsule.

In some embodiments, the present invention provides a process for obtaining a thick and dense coating on a stable water insoluble core, using in some embodiments inorganic oxide nanoparticles in combination with a sol-gel precursor, wherein the addition of phase changing material incorporated into said core provides further stability parameters to the encapsulated active agents and to the pharmaceutical composition comprising them.

Thus, in one aspect of the present invention, there is provided a process for preparing microcapsules having a core encapsulated within an inorganic oxide shell, said process comprising:
(a) preparing an oil-in-water emulsion by emulsification of an oily phase comprising at least one active agent and at least one phase changing material, in an aqueous phase, wherein at least one of said oily phase and aqueous phase comprise a sol-gel precursor;
(b) subjecting said emulsion to microcapsule forming conditions; thereby obtaining said microcapsules.

In one embodiment, this invention provides a process for preparing microcapsules having a core encapsulated within an inorganic oxide shell, said process comprising:
(a) preparing an oil-in-water emulsion by emulsification of an oily phase comprising at least one active agent and at least one phase changing material, in an aqueous phase, wherein at least one of said oily phase and aqueous phase comprise a sol-gel precursor;
(b) adjusting the pH of the emulsion to be in the range of 3 to 5; and
(c) subjecting said emulsion to microcapsule forming conditions; thereby obtaining said microcapsules;
wherein said core comprises at least one active agent and at least one phase changing material which are both surrounded by an inorganic oxide shell.

In the present invention, the term "core" refers to the inside part of the microcapsules comprising at least one active agent and at least one phase changing material that are both surrounded by an inorganic oxide shell of a microcapsule. It should be noted that additional compounds may be present in said core, including for example carriers, excipients, pharmaceutically acceptable polymers or salts etc, all in accordance with the intended use of produced microcapsules, which will be apparent to a skilled artisan preparing said microcapsules. The core of said microcapsule of the invention may comprise said at least one active agent and at least one phase changing material.

In some embodiments the viscosity of said core at room temperature may be about 300 cP, 350 cP, 400 cP, 450 cP, 500 cP, 550 cP, 600 cP, 650 cP, 700 cP, 750 cP, 800 cP, 900 cP, 1000 cP, 2000 cP, 3000 cP, 4000 cP, 5000 cP, 6000 cP, 7000 cP, 8000 cP, 9000 cP, 10,000 cP, 20,000 cP, 30,000 cP, 40,000 cP, 50,000 cP, 60,000 cP, 70,000 cP, 80,000 cP, 90,000 cP, 100,000 cP, 200,000 cP, 300,000 cP, 400,000 cP, 500,000 cP, 600,000 cP, 700,000 cP, 800,000 cP, 900,000 cP or 1,000,000 cP (when measured under various conditions). In some embodiments the viscosity of said core at room temperature is between about 300 to 600 cP. In other embodiments, the viscosity of said core at room temperature is between about 400 to 500 cP. In further embodiments, the viscosity of said core at room temperature is between about 300 to 10,000 cP. In other embodiments, the viscosity of said core at room temperature is between about 5,000 to 1,000,000 cP. In some further embodiments, the viscosity of said core at room temperature is between about 20,000 to 1,000,000 cP.

In other embodiments of the invention, said core may be solid at room temperature. In other embodiments, said core may be in a semi-solid phase at room temperature.

The oily phase utilized by a process of the invention comprises at least one active agent and at least one phase changing material. Said at least one active agent may be in a form of a water insoluble liquid or dispersion in water-insoluble liquid comprising said at least one active agent.

The oily phase may be constituted by a liquid water-insoluble active agent; which may comprise a first, liquid water-insoluble active agent dissolved and/or dispersed in a second, water insoluble liquid being another active agent or serving as a carrier. In another embodiment, said oily phase may comprise a solid active agent dissolved and/or dispersed in a water-insoluble liquid, being another active ingredient or serving as a carrier.

The term "water insoluble liquid" or "dispersion in water-insoluble liquid" refers to a solubility of the liquid (including the ingredients included therein, dissolved and/or dispersed) in water of about less than 1%/w/w, preferably 0.5% w/w and most preferably 0.15% w/w at room temperature (20-25° C.).

Accordingly, the constituents included in the core whether solid or liquid ingredients have a solubility of about less than 1% w/w, preferably 0.5% w/w and most preferably 0.15% w/w at room temperature (20-25° C.). The water insoluble liquid may be for example squalane oil, polydimethylsiloxane, mineral oil, castor oil, aromatic 200, and mixtures thereof.

In the present invention, the term "sol-gel precursor" refers to any metal or semi-metal organo-metallic monomer, or a prepolymer (which means several monomers polymerized together) thereof, which allows to obtain a glass or ceramic material by in-situ polymerization (an inorganic sol-gel polymerization process). Preferably the sol-gel precursor is a metal or semi-metal organo-metallic monomer (e.g. a metal or semi-metal alkoxide monomer).

In the present invention, the term "active agent" refers to any molecule or substance that can be used in medicine or cosmetics, and which grants the final product (cosmetics, drug, etc.), at least one desired property. In some embodiments, one active agent is encapsulated within said microcapsule obtained by the process of the invention. In other embodiments, at least two different active agents are encapsulated within said microcapsule obtained by the process of the invention. In other embodiments, said at least two different active agents are each encapsulated within a separate microcapsule, obtained either independently or simultaneously by the process of the invention.

As used herein the term "inorganic oxide salt" refers in one embodiment to metal oxide salt, in another embodiment, to semi-metal oxide salt, and in another embodiment, to a metalloid oxide salt. In some embodiments, the inorganic oxide salt is selected from sodium silicate, potassium silicate, sodium aluminate, potassium aluminate, sodium titanate, potassium titanate, sodium zirconate, potassium zirconate, and mixtures thereof. In some other embodiments, the inorganic oxide salt is a silicate salt. In some embodiments, the inorganic oxide is selected from silica, titania, alumina, zirconia, ZnO, and mixtures thereof. In further embodiments, the inorganic oxide is silica.

As used herein the term "inorganic oxide nanoparticles" refers to substantially pure metal oxide nanoparticles consisting essentially of or comprised wholly of metal oxide or a semi metal oxide. In some embodiments, metal oxide nanoparticles do not include organic material, in particular not polystyrene. According to an embodiment of the present invention, said inorganic oxide nanoparticles are selected from Silica, Titania, Zirconia, ZnO, and any mixtures thereof.

The term "phase changing material" (PCM) is meant to encompass any substance capable of changing its state of matter (phase), or at least its viscosity, in accordance with the temperature it is exposed to. PCMs typically have a high heat of fusion which enables them to melt and solidify at certain temperatures, and are capable of storing and releasing large amounts of energy. Heat is absorbed or released when the PCM material changes from solid to liquid and vice versa. When PCMs reach the temperature at which they change phase or viscosity (for example their melting temperature), they absorb large amounts of heat at an almost constant temperature. The PCM continues to absorb heat without a significant raise in temperature until all the material is transformed to the liquid phase. When the ambient temperature around a liquid material falls, the PCM solidifies, releasing its stored latent heat.

In accordance with an embodiment of the present invention, a phase changing material utilized by a process of the invention is an organic material, which is non-reactive with any compound utilized by a process of the invention and is characterized by the fact that at room temperature said PCM has a viscosity of between about 300 cP to 1,000,000 cP (when measured under various conditions).

In some embodiments, the viscosity of said PCM at room temperature may be 300 cP, 350 cP, 400 cP, 450 cP, 500 cP, 550 cP, 600 cP, 650 cP, 700 cP, 750 cP, 800 cP, 900 cP, 1000 cP, 2000 cP, 3000 cP, 4000 cP, 5000 cP, 6000 cP, 7000 cP, 8000 cP, 9000 cP, 10,000 cP, 20,000 cP, 30,000 cP, 40,000 cP, 50,000 cP, 60,000 cP, 70,000 cP, 80,000 cP, 90,000 cP, 100,000 cP, 200,000 cP, 300,000 cP, 400,000 cP, 500,000 cP, 600,000 cP, 700,000 cP, 800,000 cP, 900,000 cP or 1,000,000 cP (when measured under various conditions).

In one embodiment, said at least one phase changing material is selected from natural or synthetic paraffins (e.g. having a molecular formula of $C_nH_{2n+2}$, wherein n=10-100), $C_{10}$-$C_{100}$ alkane, $C_{10}$-$C_{100}$ alkene (having at least one double bond), $C_{10}$-$C_{100}$ alkyne (having at least one triple bond), aliphatic alcohols (e.g. having a molecular formula of $CH_3(CH_2)_nOH$ n=10-100) and fatty acids (e.g. having a molecular formula of $CH_3(CH_2)_nCOOH$ n=10-100), or any combination thereof.

In some embodiments, said at least one phase changing material is at least one natural or synthetic paraffin. In some embodiments, said at least one phase changing material is a $C_{10}$-$C_{100}$ aliphatic alcohol (in other embodiments $C_{10}$, $C_{20}$, $C_{30}$, $C_{40}$, $C_{50}$, $C_{60}$, $C_{70}$, $C_{80}$, $C_{90}$ to $C_{100}$ aliphatic alcohol). In further embodiments said at least one phase changing material is a $C_{10}$-$C_{100}$ aliphatic fatty acid (in other embodiments $C_{10}$, $C_{20}$, $C_{30}$, $C_{40}$, $C_{50}$, $C_{60}$, $C_{70}$, $C_{80}$, $C_{90}$ to $C_{100}$ aliphatic fatty acid).

In one embodiment said PCMs are liquified (or at least become substantially or partially liquified, pliable or semisolid, and capable of being handled by a process of the invention) at a temperature range of between about 35° C. to about 60° C., more preferably in a temperature range of between about 35° C. to about 45° C.

Examples of phase changing materials capable of being used by the processes of the invention include, but are not limited to: Carnauba wax (m.p. 82-86° C.), Beeswax pure (m.p. 61-65° C.), Beeswax white pure, (m.p. 61-65° C.), Beeswax bleached technical (m.p. 61-65° C.), Montan wax bleached (m.p. 80-86° C.), Montan wax bleached, partially saponified (m.p. 99-105° C.), Montanic acid (m.p. 81-87° C.), Hydrocarbon wax synthetic (m.p. 106-114° C.), Microcrystalline wax (m.p. 89-95° C.), Microcrystalline wax (m.p. 76-82° C.), Hardwax partially saponified (m.p. 104-109° C.), Beeswax yellow (m.p. 61-66° C.), Polishing Wax (m.p. 78-84° C.), Castor wax (m.p. 83-89° C.), Microwax (m.p. 89-95° C.), Microwax (m.p. 80-86° C.), Microwax (m.p. 76-82° C.), Ozokerite (m.p. 72-79° C.), Microcrystalline wax, plastic (m.p. 76-82° C.), Microcrystalline wax, soft (m.p. 74-80° C.), Wax blend (m.p. 62-68° C.), Polyolefin wax (m.p. 65-75° C.), Lanolin, Shellac, Bayberry wax (m.p. 45° C.), Candelilla wax (m.p. 67-79° C.), Ouricury wax, Rice bran wax (m.p. 77-86° C.), Soy candle (wax), Paraffin (m.p. 47-64° C.), Chinese wax, and any combinations thereof.

In one embodiment of a process of the invention, said at least one phase changing material is in a liquid state. Thus, prior to the addition of said at least one PCM, its temperature is raised until it is substantially homogenously liquified. In a further embodiment of the present invention, a process of the invention is carried out under a temperature wherein said at least one phase changing material is in a liquid state, throughout the entire emulsification and encapsulation process disclosed herein above and below. It is noted that said at least one PCM utilized by a process of the present invention, is selected such that its heat of fusion allows for processes of the invention to be carried out substantially without compromising the active agents used, the emulsion formed and the inorganic oxide shell produced for the microcapsules of the invention.

In one embodiment of the present invention, at least one inorganic oxide nanoparticle is added to said aqueous phase prior, during, or after emulsification of step (a).

In a further embodiment of a process of the invention, the process further comprises a step of cooling obtained microcapsules to room temperature. It is noted that upon cooling of said obtained microcapsules, the viscosity of said core, comprising said at least one active agent and at least one PCM, changes to have values of between about 300 cP to 1,000,000 cP (when measured under various conditions). It should be understood that such PCMs used by a process of the invention, are accumulated in the core of obtained microcapsules, and are not incorporated in any part of the inorganic-oxide shell formed by encapsulation process of the invention.

It is further noted that such microcapsules obtained by a process of the invention, demonstrate a higher stability, as measured in the amount of leakage measured upon long term storage of said microcapsules.

In some embodiments of the invention, microcapsules obtained by a process of the invention are stable for a period of at least 2 weeks at room temperature. In some embodiments of the invention, microcapsules obtained by a process of the invention are stable for a period of at least 2 months at room temperature. In some embodiments of the invention, microcapsules obtained by a process of the invention are stable for a period of between about 2 weeks to 2 years at room temperature. In other embodiments, microcapsules obtained by a process of the invention are stable for a period of between about 2 months to about 2 years at room temperature. In this context, it should be noted that a stability of a microcapsule of the invention, obtained by a process of the invention, is measured by the ability of said microcapsule to substantially maintain said at least one active agent within said microcapsule, with a maximal leakage of between about 0 to 5% of said active agent, for a set period of time under conditions of temperature and RH specified.

In a further embodiment of a process of the invention, said microcapsules encapsulating said at least one active agent and at least one phase changing material have a viscosity of between about 300 cP to about 1,000,000 cP.

According to an embodiment of the present invention, said core comprises a pharmaceutical agent, cosmetic agent, or agrochemical agent.

Additionally, according to an embodiment of the present invention, said core comprises a dermatological agent.

Further, according to an embodiment of the present invention, said dermatological agent is selected from anti-fungal agents, anti-bacterial agents, anti-inflammatory agents, anti-pruritic agents, anti-psoriatic agents, anti-acne agents, anti-rosacea agents, and any combinations thereof.

In some embodiments, an anti-acne agent is selected from benzoyl peroxide, retinoid, and mixtures thereof. The retinoid may be for example tretinoin (all trans retinoic acid, ATRA), tazarotene, iso-tretinoin, adapalene or mixtures thereof.

According to another embodiment of the present invention, said inorganic oxide nanoparticles have a particle size diameter (d50) in the range of 1-100 nm. In other embodiments particle size diameter (d50) is in the range of 1-50 nm, more preferably 5-30 nm.

By the term "particle size diameter (d50) in the range of 1-100 nanometer" is meant to encompass particles of which at least 50% by volume have diameters in the range of 1-100 nanometer.

Unless otherwise indicated, the nanoparticle size will be given using the $D_{90}$ value, i.e. the size of at least 90% of said particles (measured by volume). Thus, for example, when referring to nanoparticles having a diameter of at least about 10 nm, it should be understood to mean that the $D_{90}$ value of said nanoparticles is 10 nanometers. $D_{90}$ values may be measured by laser diffraction.

According to another embodiment, a process of the present invention further comprising adding at least one inorganic oxide salt to said aqueous phase either prior, during, or after emulsification in step (a). In another embodiment, said inorganic oxide salt is selected from sodium silicate, potassium silicate, sodium titanate, potassium titanate, sodium zirconate, potassium zirconate, and mixtures thereof. In another embodiment, the weight ratio between inorganic oxide nanoparticles and inorganic oxide salt is in the range 99:1 to 1:2, preferably 50:1 to 2:1, more preferably 50:1 to 10:1.

According to an embodiment, the process of the present invention further comprising adding a binding or cross-linking additive selected from a polymeric agent, a di- or tri-valent metal salt, a polyelectrolyte, and mixtures thereof, to said aqueous phase either prior, during, or after emulsification of step (a). It is noted that when using this type of binding or cross-linking additive, the prepared microcapsules will have a more cross-linked and stronger inorganic oxide shell.

In one embodiment, said polymeric agent is selected from sodium alginate, polyvinyl alcohol, carboxymethyl cellulose, polyvinyl pyrrolidone, and mixtures thereof.

In another embodiment, said di- or tri-valent metal salt is selected from aluminum sulfate, sodium aluminate, sodium borate, calcium chloride, and mixtures thereof.

Without being bound to theory, the binding or cross-linking additives may provide such strengthening and cross-linking properties of microcapsules shell as follows:

Aluminum sulfate—the positively charged aluminum cations may be attracted to the negatively charged metal oxide nanoparticles and as such may work as cross-linkers between the inorganic oxide nanoparticles which are adsorbed on the oil droplet-water interface.

Sodium aluminate—sodium aluminate may react with the silanol groups on the inorganic oxide nanoparticles surface, and as such may work as cross-linkers between the inorganic oxide nanoparticles, which are adsorbed on the oil droplet-water interface.

PVA (polyvinyl alcohol) may adsorb onto the inorganic oxide shell via hydrogen bonds and also can be cross-linked by sodium borate.

Sodium borate—sodium borate may cross-link the PVA with the inorganic oxide shell of the microcapsules.

Sodium alginate—sodium alginate may adsorb onto the inorganic oxide shell (produced from adsorption of inorganic oxide nanoparticles) and may be cross-linked by addition of calcium chloride.

PDAC 7 (polyquaternium 7)—PDAC 7 may be used for coating of the inorganic oxide shell. PDAC 7 which is positively charged may adsorb onto the negatively charged inorganic oxide shell and as such decrease the "gaps" between the inorganic oxide nanoparticles and thus strengthen the shell.

CMC (carboxymethyl cellulose)—CMC may be used for additional coating of the inorganic oxide shell. It can be used after coatings with PDAC 7.

In one embodiment, said polyelectrolyte is selected from Polyquaternium-7 (Dimethyldiallylammonium chloride acrylamide copolymer), Polyquaternium-[Poly[(dimethyliminio)-2-butene-1,4-diyl chloride],α-[4-[tris(2-hydroxyethyl)ammonio]-2-butenyl]-ω-[tris(2-hydroxyethyl)ammonio]-, dichloride], Polyquaternium-10 [Cellulose 2-hydroxyethyl2-(2-hydroxy-3-(trimethylammonio) propoxy)ethyl-2-hydroxy-3-(trimethylammonio)propyl ether, chloride], Chitosan, Polylysine, and mixtures thereof.

According to one embodiment, at least one of said oily and aqueous phases, comprise at least one surfactant. In one embodiment, said surfactant is selected from a cationic surfactant, an anionic surfactant, a non-ionic surfactant and mixtures thereof. In one embodiment, the at least one surfactant is a cationic surfactant. In a further embodiment, said at least one cationic surfactant is cetyltrimethyl ammonium chloride (CTAC).

In another embodiment, said oily phase may comprise a hydrophobic surfactant, hydrophobic polymeric surfactant, or mixtures thereof. In one embodiment, the hydrophobic surfactant or hydrophobic polymeric surfactant is a non-ionic surfactant. The hydrophilic surfactant may be for example an anionic, a cationic, a non-ionic surfactant, or mixtures thereof.

In some embodiments, the concentration of the cationic surfactant in the aqueous phase may be from 0.1 to 5% (w/w), in other embodiments, from 1 to 5% (w/w). It is appreciated that the concentration of the surfactant will also depend on the percentage of the oily phase and aqueous phase. In some embodiments, the concentration of the surfactant may be 5-10% (w/w) from the weight of the oily phase.

According to another embodiment of the present invention, said oily phase comprises a sol-gel precursor.

According to a further embodiment of the present invention, said sol-gel precursors are selected from metal alkoxide monomers, semi-metal alkoxide monomers, metal ester monomers, semi-metal ester monomers and from monomers of the formula $M(R)_n(P)_m$, wherein M is a metallic or semi metallic element, R is a hydrolysable substituent, n is an integer from 2 to 6, P is a non-polymerizable substituent and m is and integer from 0 to 6, a partially hydrolyzed and partially condensed polymer of any of the above, and mixtures of any of the above. In one embodiment, said metallic or semi metallic element is selected from Si, Ti, Zr, Al, and Zn.

In another embodiment, said sol-gel precursors are selected from silicon alkoxide monomers, silicon ester monomers, monomers of the formula $Si(R)_n(P)_m$, wherein R is a hydrolysable substituent, n is an integer from 2 to 4, P is a non-polymerizable substituent and m is an integer from 0 to 4, a partially hydrolyzed and partially condensed polymer of any of the above, and mixtures of any of the above. In one embodiment, said silicon alkoxide monomer is selected from tetramethoxy silane, tetraethoxy silane, and mixtures thereof. In a further embodiment, said monomers of the formula $Si(R)_n(P)_m$ are selected from methyl trimethoxysilane, dimethyl dimethoxysilane, and mixtures thereof. In yet a further embodiment, said sol-gel precursor is a monomer (e.g. a metal alkoxide monomer, a semi-metal alkoxide monomer) as described hereinbefore.

According to an embodiment of the present invention, the pH of said aqueous phase is in the range 2-9. In another embodiment, the pH of said aqueous phase is in the range 2-7, even more preferably the pH is in the range 3-5.

According to an embodiment of the present invention, said microcapsule forming conditions comprise isolating the microcapsules through procedures selected from at least one of: separation by centrifuge, filtration, evaporation, re-suspension in aqueous medium, and dialysis. In another embodiment of the present invention, said microcapsules forming conditions comprise altering the pH of the formed emulsion to a range of between about 2 to about 9, preferably the pH is in the range 3-5.

According to another embodiment of the present invention, said microcapsule forming conditions comprise stirring of said emulsion. In some embodiments, said stirring may be for example by mechanical stirrer at 200-500 rpm.

According to another embodiment of the present invention, said microcapsule forming conditions comprise drying the obtained microcapsules in suspension.

According to another embodiment, the product obtained by a process of the invention is a suspension of said formed microcapsules.

According to a further embodiment of the present invention, the product obtained by a process of the invention is a powder of said microcapsules.

In another aspect of the present invention there is provided microcapsules obtainable by the process of the present invention.

Yet, in another aspect of the present invention, there is provided microcapsules comprising a core encapsulated by an inorganic oxide shell, wherein said core has a viscosity of between about 300 cP to about 1,000,000 cP (when measured under various conditions); wherein the thickness of said inorganic oxide shell is in the range of 0.02-10 micron, preferably in the range of 0.05-1 micron; and wherein said shell is obtained from (a) inorganic oxide nanoparticles, and (b) a hydrolyzed and polymerized sol gel precursor. In another embodiment, the thickness of said inorganic oxide shell is in the range of 0.1-10 micron.

In some embodiments, the viscosity of said core at room temperature may be 350 cP, 400 cP, 450 cP, 500 cP, 550 cP, 600 cP, 650 cP, 700 cP, 750 cP, 800 cP, 900 cP, 1000 cP, 2000 cP, 3000 cP, 4000 cP, 5000 cP, 6000 cP, 7000 cP, 8000 cP, 9000 cP, 10,000 cP, 20,000 cP, 30,000 cP, 40,000 cP, 50,000 cP, 60,000 cP, 70,000 cP, 80,000 cP, 90,000 cP, 100,000 cP, 200,000 cP, 300,000 cP, 400,000 cP, 500,000 cP, 600,000 cP, 700,000 cP, 800,000 cP, 900,000 cP or 1,000,000 cP (when measured under various conditions).

It is noted that viscosity value measurement depends on the instrument of measurement, spindle used, speed and temperature of measurement. Unless otherwise mentioned, the viscosity measurements given in the present invention were measured using a Brookfield LVDV-II+Pro viscometer equipped with a small sample adaptor, spindle #21 at 6 RPM and temperature of 30° C.

In some embodiments, a microcapsule of the invention is capable of being stable (i.e. maintain at least about 0 to 5% of said encapsulated at least one active agent) for a period of between about 2 weeks to about 2 years at room temperature. In other embodiments, a microcapsule of the invention is capable of being stable for a period of between about months to about 2 years at room temperature. In other embodiments, a microcapsule of the invention is capable of being stable for a period of at least 2 weeks at room temperature. In further embodiments, a microcapsule of the invention is capable of being stable for a period of at least 2 months at room temperature.

Further, according to another embodiment of the invention, the inorganic oxide shell has a width (thickness) of about 0.1, 0.2, 0.3, 0.4, 0.5, 0.6, 0.7, 0.8, 1, 1.5, 2 or 5 micron or above, preferably up to 10 micron. The core, shell, etc. constituents may be as described in the present invention.

The width of the inorganic oxide layer may be determined for example by a Transmission Electron Microscope or Confocal Microscope such that in a circular cross sectional area of the microcapsules the smallest width is at least e.g. 0.1 micron (the width is determined as the smallest distance from the outer surface of the microcapsules (i.e. inorganic oxide surface) to the core-inorganic oxide interface).

In another aspect of the present invention, there is provided a composition comprising microcapsules of the present invention.

Further, in another aspect of the present invention, there is provided a method for treating a surface condition in a subject in need thereof comprising topically administering to said subject a composition of the present invention, wherein the core material comprises a dermatological agent.

The term "treating" or "treatment" as used herein includes any treatment of a condition, disease or disorder associated with a patient's body surface such as the skin or mucosal membrane, and includes inhibiting the disease or disorder (i.e. arresting its development), relieving the disease or disorder (i.e. causing regression of the disease or disorder), or relieving the conditions caused by the disease (i.e. symptoms of the disease). The concentrations of the dermatological agents that can be used for treatment of a specific disease or disorder may be as described in The Merck index an encyclopedia of chemical drugs and biologicals, Rahway, N.J.; Merck & Co; 1989, incorporated herein by reference in its entirety.

Although individual needs may vary, determination of optimal ranges for effective amounts of the compositions is within the skill of the art. Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s).

When referring to pharmaceutical compositions, comprising a compound of the subject invention, it should be understood to encompass admixtures of microcapsules of the invention, with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intrathecal) administration or administration via an implant. The compositions may be prepared by any method well known in the art of pharmacy.

Such methods include the step of bringing in association compounds used in the invention or combinations thereof with any auxiliary agent.

Auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragees or capsules, or as a powder or granules, or as a solution or suspension. The composition may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injections. The compositions may be presented in unit-dose or multi-dose containers, for example sealed vials and ampoules, and may be stored in a freeze-dried (lyophilised) condition requiring only the addition of sterile liquid carrier, for example water, prior to use.

For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

According to an embodiment of the present invention, said surface is skin or mucosal membrane.

According to another embodiment of the present invention, said surface condition is a skin disease or disorder selected from acne, infection, inflammation, pruritus, psoriasis, seborrhea, contact dermatitis, rosacea, and a combination thereof.

Additionally, in another aspect of the present invention, there is provided a composition comprising microcapsules as described in the present invention, wherein the core comprises a dermatological agent, for treatment of a disease or disorder selected from acne, infection, inflammation, pruritus, psoriasis, seborrhea, contact dermatitis, rosacea, and a combination thereof.

Yet, in another aspect, there is provided a use of the microcapsules of the present invention, wherein said core comprises a dermatological agent for the preparation of a topically administered composition.

According to an embodiment of the invention, said topical administration is for treating a disease or disorder selected from acne, psoriasis, seborrhea, contact dermatitis, infection, rosacea, inflammation, and a combination thereof.

In another aspect of the present invention, there is provided a composition for pest control comprising the microcapsules of the invention, wherein said core comprises a pesticide. In one embodiment of the present invention, said pesticide is selected from a herbicide, an insecticide, a fungicide, and mixtures thereof.

According to yet another embodiment of the present invention, said composition is for use in crop protection or non-crop pest control.

DETAILED DESCRIPTION OF EXEMPLARY EMBODIMENTS

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Unless otherwise indicated "%" refers to weight per weight (w/w) %.

"BPO (75%)" refers to 75% w/w BPO (Benzoyl peroxide) with 25% w/w water.

"Ludox® TM 50 (50%)" refers to a dispersion of silica nanoparticles (average particle size diameter of about 20-30 nm) in water (50% w/w in water). Ludox TM 50 was obtained from Sigma-Aldrich, Israel.

"Ludox® AM-30" refers to colloidal silica stabilized with sodium aluminate and dispersed in water (30% w/w in water).

Ludox® AM-30 was obtained from Sigma-Aldrich, Israel.

"CTAC (29%)" refers to a solution of cetyl trimethyl ammonium chloride 29% w/w in water.

"PVA (10%)" refers to a solution of polyvinyl alcohol 10% w/w in water.

"sodium silicate (25%)" refers to a solution of sodium silicate 25% w/w in water.

"GMIS" refers to glyceryl monoisostearate. GMIS was obtained from Scher Chemicals, USA.

"aluminum sulfate solution (50%)" or "aluminum sulfate (50%)" refers to a solution of aluminum sulfate decaoctahydrate 50% w/w in water.

"PDAC 7 (5%)" refers to a solution of polyquaternium 7 (Diallyldimethylammonium chloride/acrylamide copolymer), 5% w/w in water.

"CMC (10%)" refers to a solution of sodium salt of carboxymethyl cellulose 10% w/w in water.

"sodium aluminate (50%)" refers to solution of sodium aluminate 50% w/w in water.

"sodium borate (5%)" refers to solution of sodium borate 5% w/w in water.

"sodium alginate (5%)" refers to solution of sodium alginate 5% w/w in water.

"Beeswax" refers to Beeswax pure (m.p. 61-65° C.), Beeswax white pure, (m.p. 61-65° C.), Beeswax bleached technical (m.p. 61-65° C.).

"PVPK30 (40%)" refers to solution of PVP K30 (Polyvinylpyrrolidone K-30) 40% w/w in water.

EXAMPLES

Example 1: Encapsulation Process ATRA (E-ATRA)

Core-Shell Step
1. Aqueous phase (phase A): 2.53 g CTAC (30.7%) and 386.27 g WFI were stirred with a magnetic stirrer to homogeneity.
2. Beeswax ingredient: 30.0 g Beeswax, heated to 70° C. until Beeswax was liquid.

3. Oil phase: 90.0 g TEOS, and 97.01 g Squalane were stirred with a magnetic stirrer to dissolution. 30.0 g ATRA were added to solution and stirred, using same magnetic stirrer, for additional 10 min and milled in Dynomill at 5000 rpm for 10 min. Milled oil phase was heated to 55° C. under magnetic stirring, using a water bath.
4. Aqueous phase was heated to 55° C. under magnetic stirring, using a water bath.
5. In a IL beaker, 91.37 g milled oil phase and 5.83 g Beeswax, were mixed for 5 minutes at 55° C. under magnetic stirring, using a water bath (phase B).
6. Phase C: 14.0 g Sodium silicate solution (25%) and 30.0 g HCl 5N.
7. Phase B mixed under high shear mixing at 4000 rpm (Polytron 6100).
8. Phase A was added to Phase B and mixed with high shear at 4000 rpm for 1 min. after which high shear speed was reduced to 3000 rpm.
9. Phase C was added until pH 7.0+0.2 was reached.
10. HCl 5N was added to emulsion until pH 3.0+0.2 was reached.
11. Emulsion was mixed with high shear for additional 2 min at 3000 rpm.
12. Emulsion was stirred for 17 hr. at 50° C. at 80 rpm and then cool to 25° C. until core-shell suspension was achieved.

Coating Step (Optional)

13. 150.0 g of core-shell suspension was placed under high-shear at 2500 rpm.
14. 5% NaOH 5N were added until pH 5.0+0.2.
15. 1.2 g PDAC-7 (3%) was added and mixture was stirred for 1 min.
16. 1.2 g Sodium silicate (25%) was added and pH adjusted to 5.0+0.2 with HCl 5N solution, and mixture was stirred for 1 min. (1st cycle).
17. Coating cycle (steps 15-16) was repeated at least 10 times.

The viscosity of the core of the obtained microcapsules was measured to be between 475 to 565 cP (as measured using a Brookfield LVDV-II+Pro viscometer equipped with a small sample adaptor, spindle #21 at 6 RPM and temperature of 30° C.).

Example 2—Encapsulation of BPO (Benzoyl Peroxide) (BPO Dispersed in DC-246)

a) Preparing the oil phase: A mixture of 67.68 g BPO (75%), 132.04 g DC-246 (cyclohexasiloxane, Dow Corning, USA) and 10.06 g Span 65 as dispersant agent and 45.6 g of TEOS (tetraethoxy silane) were milled first by high shear at 4000 rpm for 2 minutes and then by microfluidizer for 15 minutes.
b) Preparing the water phase: An aqueous phase including 6.06 g of Myrj 45 (polyoxyethylene (8) stearate), 2.68 g CTAC (29%), 64.54 g PVA (10%) and 328.13 g of water was prepared.

The oil phase (a) was added to the water phase (b) under shearing at 6000 rpm for 2 minutes. Then, 49.93 g of Ludox® TM 50 (50%) and 5 ml of sodium silicate (25%) were added, and then the pH was adjusted to 3. The mixture was transferred to reactor and stirred for 20 h.

Example 3—Encapsulation of BPO (BPO Dispersed in DC-350)

a) Preparing the oil phase: A mixture of 67.49 g BPO (75%), 130.92 g DC-350 (polydimethylsiloxane, obtained from Dow coming, USA) and 10.16 g cetyl alcohol as dispersant agent and 45.42 g of TEOS were milled first by high shear at 4000 rpm for 2 minutes and then by microfluidizer for 15 minutes.
b) Preparing the water phase: A water phase including 5.69 g of Myrj 45 (polyoxyethylene (8) stearate), 2.25 g CTAC (29%), 65.05 g PVA (10%) and 327.24 g of water, was prepared.

The two phases were preheated at 50° C. and then the oil phase (a) was added to the water phase (b) under shearing at 5000 rpm for 2 minutes. Then, 50.09 g of Ludox® TM 50 (50%) were added and the solution became viscous. Then, 5 ml of sodium silicate (25%) was diluted up to 100.09 g with water and the resulted solution was added to the viscous mixture under shearing of 5000 rpm for 1 minute. The pH was adjusted to 3 and then the mixture was transferred to reactor and stirred for 20 h.

Example 4—Encapsulation of BPO (BPO Dispersed in Squalane)

a) Preparing the oil phase: A mixture of 68.64 g BPO (75%), 129.58 g squalane (obtained from Lake Oil, Spain) and 5.08 g GMIS as dispersant agent and 89.85 g of TEOS were milled first by high shear at 10000 rpm for 2 minutes and then by microfluidizer for 15 minutes.
b) Preparing the water phase: A water phase including 1.18 g CTAC (29%), 65.10 g PVA (10%) and 329.93 g of water, was prepared.

The oil phase (a) was added to the water phase (b) under shearing at 5000 rpm for 30 seconds. Then, 49.64 g of Ludox® TM 50 (50%) was added and shearing continued further 30 seconds. Then, 20.72 g of aluminum sulfate solution (50%) were added and the obtained pH was 3. The mixture was transferred to reactor preheated at 40° C. and the mixture was stirred at 118 rpm for 4 hours. Then, the temperature was decreased to room temperature and stirring continued for 20 h.

Example 5—Encapsulation of BPO (BPO Dispersed in Squalane)

a) Preparing the oil phase: A mixture of 80.63 g BPO (75%), 108.15 g squalane (obtained from Lake Oil, Spain) and 5.71 g GMIS as dispersant agent and 27.97 g of TEOS were milled first by high shear at 10000 rpm for 1 minute and then by microfluidizer for 15 minutes.
b) Preparing the water phase: A water phase including 1.02 g CTAC (29%), 60.27 g PVA (10%) and 290.09 g of water, was prepared.

The oil phase (a) was added to the water phase (b) under shearing at 5000 rpm for 30 seconds. Then, 30.58 g of Ludox® TM 50 (50%) was added and shearing continued further 30 seconds. Then, 20.09 g of aluminum sulfate solution (50%) were added under shearing for 30 seconds and the obtained pH was 3.2. The mixture was transferred to reactor preheated at 40° C. and the mixture was stirred at 100 rpm for 4 hours. Then, the temperature was decreased to room temperature and stirring continued for 20 h.

Example 6—Encapsulation of BPO (BPO Dispersed in Squalane)

a) Preparing the oil phase: A mixture of 53.19 g BPO (75%), 75.21 g squalane and 5.12 g GMIS as dispersant agent and 80.68 g of TEOS were milled first by high shear at 10000 rpm for 1 minute and then by microfluidizer for 15 minutes.

b) Preparing the water phase: A water phase including 4.16 g CTAC (29%), 6.5 g PVA (10%) and 280.45 g of water, was prepared.

The oil phase (a) was added to the water phase (b) under shearing at 5000 rpm for 30 seconds. Then, 90.11 g of Ludox® TM 50 (50%) was added and shearing continued further 30 seconds. Then, 9.96 g of aluminum sulfate dissolved in 15.19 g water were added and the resulted mixture was milled at 6100 rpm for 1 minute. The mixture was then transferred to reactor preheated at 38.8° C. and it was stirred at 118 rpm for 4 hours. Then, the temperature was decreased to room temperature and stirring continued for 20 h.

Example 7—Encapsulation of BPO (BPO Dispersed in Squalane)

a) Preparing the oil phase: A mixture of 106.35 g BPO (75%), 88.09 g squalane and 4.91 g GMIS as dispersant agent and 41.05 g of TEOS were milled first by high shear at 10000 rpm for 1 minute. A thick mixture was obtained and it could not be milled by microfluidizer.

b) Preparing the water phase: A water phase including 1.31 g CTAC (29%), 6.3 g PVA (10%) and 283.1 g of water, was prepared.

The oil phase (a) was added to the water phase (b) under shearing at 5000 rpm for 30 seconds. Then, 60.66 g of Ludox® TM 50 (50%) was added and shearing continued further 30 seconds. Then, 50.18 g of aluminum sulfate (50%) were added and the resulted mixture was milled at 6000 rpm for 1 minute. The mixture was then transferred to reactor preheated at 41.8° C. and it was stirred at 100 rpm for 4 hours. Then, the temperature was cooled down to room temperature and stirring continued for 20 h.

Example 8—Encapsulation of BPO (BPO Dispersed in Squalane)

a) Preparing the oil phase: A mixture of 106.24 g BPO (75%), 61.12 g squalane and 5.65 g cetyl alcohol as dispersant agent and 60.49 g of TEOS were milled first by high shear at 10000 rpm for 1.5 minutes. A thick mixture was obtained, and it could not be milled by microfluidizer.

b) Preparing the water phase: A water phase including 1.09 g CTAC (29%), 61.52 g PVA (10%) and 269.45 g of water, was prepared.

The oil phase (a) was added to the water phase (b) under shearing at 5000 rpm for 30 seconds. Then, 59.87 g of Ludox® TM 50 (50%) was added and shearing continued further 1 minute. Then, 21.87 g of aluminum sulfate (50%) were added and the resulted mixture was milled at 6000 rpm for 1 minute. The mixture was then transferred to reactor preheated at 40° C. and stirred for 4 hours. Then, the temperature was cooled down to room temperature and stirring continued for 20 h.

Example 9—Encapsulation of BPO (BPO Dispersed in Squalane)

a) Preparing the oil phase: A mixture of 105.28 g BPO (75%), 130.13 g squalane and 5.48 g Span 20 and 32.51 g of TEOS were milled first by high shear at 10000 rpm for 1 minute. A thick mixture was obtained, and it could not be milled by microfluidizer.

b) Preparing the water phase: An aqueous phase including 4.31 g CTAC (29%), 6.5 g PVA (10%) and 279.8 g of water, was prepared.

The oil phase (a) was added to the water phase (b) under shearing at 4000 rpm and then 90.41 g of Ludox® TM 50 (50%) was added and shearing continued 1 minute. Then, 20.88 g of aluminum sulfate (50%) were added and the resulted mixture was milled at 5000 rpm for 1 minute. The mixture was then transferred to reactor preheated at 39.2° C. and stirred at 103 rpm for 4 hours. Then, the temperature was cooled down to room temperature and stirring continued for 60 h.

Example 10—Encapsulation of BPO (BPO Dispersed in Squalane)

a) Preparing the oil phase: A mixture of 80.25 g BPO (75%), 107.04 g squalane and 5.01 g cetyl alcohol and 30.40 g of TEOS were milled first by high shear at 10000 rpm for 1 minute. A thick mixture was obtained, and it could not be milled by microfluidizer.

b) Preparing the water phase: A water phase including 4.33 g CTAC (29%), 6.16 g PVA (10%) and 279.59 g of water, was prepared.

The oil phase (a) was added to the water phase (b) under shearing at 4000 rpm and then 59.43 g of Ludox® TM 50 (50%) was added, and then the resulted mixture was homogenized at 8000 rpm for 1 minute since the mixture was very thick. Then, 49.45 g of aluminum sulfate (50%) were added and the resulted mixture was milled at 8000 rpm for 30 seconds. The mixture was then transferred to reactor preheated at 41.2° C. and stirred at 103 rpm for 4 hours. Then, the temperature was cooled down to room temperature and stirring continued for 20 h.

Example 11—Encapsulation of BPO (BPO Dispersed in Squalane)

a) Preparing the oil phase: A mixture of 80.2 g BPO (75%), 93.5 g squalane (obtained from Lake Oil, Spain) and 5.38 g Span 20 and 42.07 g of TEOS were milled first by high shear at 10000 rpm for 1 minute and then by microfluidizer for 15 minutes.

b) Preparing the water phase: A water phase including 4.05 g CTAC (29%), 61.51 g PVA (10%) and 257.74 g of water, was prepared.

The oil phase (a) was added to the water phase (b) under shearing at 4000 rpm and then 61.42 g of Ludox® TM 50 (50%) was added and shearing at 5000 rpm continued for 1 minute. Then, 21.1 g of aluminum sulfate (50%) were added and the resulted mixture was milled at 5000 rpm for 1 minute. The mixture was then transferred to reactor preheated at 41.2° C. and stirred at 103 rpm for 4 hours. Then, the temperature was cooled down to room temperature and stirring continued for 20 h.

Example 12—Formulation of Encapsulated ATRA and Encapsulated BPO (E-ATRA 0.1%/E-BPO 6%)

Ingredients:
(a) E-ATRA suspension: equivalent to 0.1% ATRA, (prepared according to the procedure in Example 1).
(b) E-BPO suspension: equivalent to 6% BPO (prepared according to the procedure in any one of Examples 2-11).

(c) Carbomer 980: 1.2% (Carbopol® 980 NF from Lubrizol)
(d) Carbomer 1342: 0.3% (Pemulen TR-2 NF from Lubrizol)
(e) Sodium hydroxide (Sodium hydroxide pellets extra pure Ph Eur, BP, JP, NF, FCC, E 524 from Merck)
(f) Water Formulation Preparation:

Carbomer 980 & carbomer 1342 were dispersed in water to a lump-free, homogeneous suspension. E-ATRA suspension was added into the carbomers suspension. E-BPO suspension was added into the carbomers suspension. Sodium hydroxide was added to achieve pH values of 5.0±0.1. Water was added to top 100% formulation weight. Formulation was finally mixed until homogeneity.

Example 13—Formulation of Encapsulated ATRA and Encapsulated BPO (E-ATRA 0.1%/E-BPO 6%)

Ingredients:
(a) E-ATRA suspension: equivalent to 0.1% ATRA, (prepared according to the procedure in Example 1).
(b) E-BPO suspension: equivalent to 6% BPO (prepared according to the procedure in any one of Examples 2-11).
(c) Carbomer 980: 1.0% (Carbopol® 980 NF from Lubrizol)
(d) Hydroxyethyl cellulose: 0.7% (Natrosol® 250 HHX PHARM hydroxyethylcellulose from Hercules).
(e) Sodium hydroxide (Sodium hydroxide pellets extra pure Ph Eur, BP, JP, NF, FCC, E 524 from Merck)
(f) Water Formulation Preparation:

Carbomer 980 & hydroxyethyl cellulose were dispersed in water to a lump-free, homogeneous suspension. E-ATRA suspension was added into suspension. E-BPO suspension was added into the suspension. Sodium hydroxide was added to achieve pH values of 5.0±0.1. Water was added to top 100% formulation weight. Formulation was finally mixed until homogeneity.

Example 14—Formulation of Encapsulated ATRA and Encapsulated BPO (E-ATRA 0.1%/E-BPO 6%)

Ingredients:
(a) E-ATRA suspension: equivalent to 0.1% ATRA, (prepared according to the procedure in Example 1).
(b) E-BPO suspension: equivalent to 6% BPO (prepared according to the procedure in any one of Examples 2-11).
(c) Hydroxyethyl cellulose: 1.25% (Natrosol® 250 HHX PHARM hydroxyethylcellulose from Hercules).
(d) Hydroxypropyl cellulose: 0.5% (Natrosol® 250 HHX PHARM hydroxyethylcellulose from Hercules).
(e) Glycerin: 15% (Glycerine 99.5% USP from Oleochemicals)
(f) Hydrochloric acid (Hydrochloric acid fuming 37% extra pure Ph Eur, BP, JP, NF from Merck)
(g) Water Formulation Preparation:

E-ATRA suspension was mixed with water. E-BPO suspension was added to E-ATRA suspension. Hydroxyethyl cellulose and hydroxypropyl cellulose were wetted with glycerin in a separate container. The wetted paste was added to the E-ATRA and E-BPO suspension. Hydrochloric acid was added to achieve a pH level of 3.5±0.1. Reminder of water was added to top up formulation to 100%. Formulation was finally mixed until homogeneity.

Example 15—Formulation of Encapsulated ATRA and Encapsulated BPO (E-ATRA 0.1%/E-BPO 6%)

Ingredients:
(h) E-ATRA suspension: equivalent to 0.1% ATRA, (prepared according to the procedure in Example 1).
(i) E-BPO suspension: equivalent to 6% BPO (prepared according to the procedure in any one of Examples 2-11).
(j) Hydroxyethyl cellulose: 1.25% (Natrosol® 250 HHX PHARM hydroxyethylcellulose from Hercules).
(k) Hydroxypropyl cellulose: 0.3% (Klucel®).
(l) Glycerin: 5% (Glycerine 99.5% USP from Oleochemicals)
(m) Hydrochloric acid (Hydrochloric acid fuming 37% extra pure Ph Eur, BP, JP, NF from Merck)
(n) Water Formulation Preparation:

E-ATRA suspension was mixed with water. E-BPO suspension was added to E-ATRA suspension. Hydroxyethyl cellulose and hydroxypropyl cellulose were wetted with glycerin in a separate container. The wetted paste was added to the E-ATRA and E-BPO suspension. Hydrochloric acid was added to achieve a pH level of 3.5±0.1. Reminder of water was added to top up formulation to 100%. Formulation was finally mixed until homogeneity.

Example 16—Stability of Formulations of Encapsulated ATRA and Encapsulated BPO (E-ATRA 0.1%/E-BPO 6%)

The following stability data was obtained from measurements of formulations of Examples 12-15 performed using Tretinoin assays were measured according to USP32, 2009 edition, page 3779—Tretinoin cream.

TABLE 1

Stability of Formulation in Example 12

| Tests | | Specification limits | Zero Time | Time | | | |
|---|---|---|---|---|---|---|---|
| | | | | 2 w | 1 month | 2 month | 3 month |
| ATRA | Assay | 0.09-0.11% | 0.107 | 0.103 | 0.099 | 0.091 | |
| | RSD, % | LT 3.0% | 0.8 | 0.8 | 0.2 | 0.9 | |
| | Sum of degradation products | collect data | 0.42 | 0.83 | 1.22 | 1.47 | |
| degradation products | RRT 0.25 | | 0.34 | 0.23 | 0.22 | 0.19 | |
| | RRT 0.56 | | | | 0.09 | 0.09 | |
| | RRT 0.86 | | | | 0.09 | 0.09 | |
| | RRT 0.921 | | | 0.07 | 0.09 | 0.09 | |
| | RRT 0.935 | | | | 0.08 | 0.09 | |

TABLE 1-continued

Stability of Formulation in Example 12

| Tests | Specification limits | Zero Time | 2 w | 1 month | 2 month | 3 month |
|---|---|---|---|---|---|---|
| RRT 0.963 | | | 0.09 | 0.09 | 0.08 | 0.08 |
| RRT 1.2 | | | | | 0.1 | 0.18 |
| RRT 1.24 | | | | 0.08 | 0.13 | 0.21 |
| RRT 1.578 | | | | 0.12 | 0.15 | 0.19 |
| RRT 1.592 | | | | 0.23 | 0.28 | 0.34 |

TABLE 2

Stability of Formulation in Example 13

| | Tests | | Specification limits | Zero Time | 8 days | 1 month | 2 month | 3 month |
|---|---|---|---|---|---|---|---|---|
| ATRA | Assay | | 0.09-0.11% | 0.106 | 0.104 | 0.099 | 0.094 | |
| | RSD, % | | LT 3.0% | 0.6 | 0.8 | 0.3 | 0.1 | |
| | Sum of degradation products | | collect data | 0.51 | 1 | 1.57 | 1.91 | |
| degradation products | RRT 0.25 | | | 0.38 | 0.32 | 0.24 | 0.19 | |
| | RRT 0.28 | | | | | | | |
| | RRT 0.56 | | | | | | | |
| | RRT 0.86 | | | | | 0.09 | | |
| | RRT 0.921 | | | | | 0.09 | 0.09 | |
| | RRT 0.935 | | | | | | | |
| | RRT 0.963 | | | 0.13 | 0.09 | | | |
| | RRT 1.2 | | | | | 0.12 | 0.2 | |
| | RRT 1.24 | | | | 0.11 | 0.23 | 0.36 | |
| | RRT 1.578 | | | | 0.2 | 0.24 | 0.29 | |
| | RRT 1.592 | | | | 0.46 | 0.66 | 0.77 | |

TABLE 3

Stability of Formulation in Example 14

| | Tests | | Specification limits | Zero Time | 2 w | 1 month | 2 month | 9 month |
|---|---|---|---|---|---|---|---|---|
| ATRA | Assay | | 0.09-0.11% | 0.107 | 0.102 | 0.1 | | |
| | RSD, % | | LT 3.0% | 0.8 | 2.5 | 0.9 | | |
| | Sum of degradation products | | collect data | 0.44 | 0.6 | 0.7 | | |
| degradation products | RRT 0.25 | | | 0.24 | 0.15 | 0.21 | | |
| | RRT 0.28 | | | | | | | |
| | RRT 0.56 | | | | | | | |
| | RRT 0.86 | | | | | | | |
| | RRT 0.921 | | | 0.1 | 0.09 | 0.12 | | |
| | RRT 0.935 | | | 0.1 | 0.09 | | | |
| | RRT 0.963 | | | | | | | |
| | RRT 1.2 | | | | | | | |
| | RRT 1.24 | | | | | | | |
| | RRT 1.52 | | | | | | | |
| | RRT 1.578 | | | | 0.11 | 0.16 | | |
| | RRT 1.592 | | | | 0.18 | 0.24 | | |

TABLE 4

Stability of Formulation in Example 15

| Tests | | Specification limits | Zero Time | 2 w | 1 month | 2 month | 9 month |
|---|---|---|---|---|---|---|---|
| ATRA | Assay | 0.09-0.11% | 0.109 | 0.107 | 0.105 | 0.104 | |
| | RSD, % | LT 3.0% | 0.7 | 0.4 | 0.2 | 0.5 | |
| | Sum of degradation products | collect data | 0.35 | 0.8 | 0.88 | 0.93 | |
| degradation products | RRT 0.25 | | | 0.25 | 0.34 | 0.27 | 0.13 |
| | RRT 0.28 | | | | | | |
| | RRT 0.56 | | | | | | |
| | RRT 0.86 | | | | | | 0.08 |
| | RRT 0.921 | | | | 0.09 | 0.12 | 0.1 |
| | RRT 0.935 | | | | | | |
| | RRT 0.963 | | 0.1 | 0.08 | | | |
| | RRT 1.2 | | | | | | |
| | RRT 1.24 | | | | | | |
| | RRT 1.52 | | | | | | |
| | RRT 1.578 | | | 0.12 | 0.21 | 0.26 | |
| | RRT 1.592 | | | 0.18 | 0.28 | 0.37 | |

TABLE 5

Stability results of Formulations 12-15 (Zero time and 40 C.)

| | Zero time | | | 40 C. 1 week | | |
|---|---|---|---|---|---|---|
| Formulation | Assay | RSD | % degrad prod | Assay | RSD | % degrad prod | % of degrad from t0 |
| Example 12 | 0.107 | 0.8 | 0.42 | 0.092 | 1 | 1.88 | 14.0 |
| Example 13 | 0.106 | 0.6 | 0.51 | 0.09 | 0.2 | 2.8 | 15.1 |
| Example 14 | 0.107 | 0.8 | 0.44 | 0.098 | 1.2 | 0.9 | 8.4 |
| Example 15 | 0.109 | 0.7 | 0.35 | 0.104 | 0.9 | 0.7 | 4.6 |

TABLE 6

Stability Results of Formulations 12-15 (25 C.)

| | 25 C. | | | | | | | | | | | |
|---|---|---|---|---|---|---|---|---|---|---|---|---|
| | 2 weeks | | | | 1 month | | | | 2 month | | | |
| Formulation | Assay | RSD | % degrad prod | % of degrad from t0 | Assay | RSD | % degrad prod | % of degrad from t0 | Assay | RSD | % degrad prod | % of degrad from t0 |
| Example 12 | 0.103 | 0.8 | 0.83 | 3.7 | 0.099 | 0.2 | 1.22 | 7.5 | 0.091 | 0.9 | 1.47 | 15.0 |
| Example 13 | 0.104 | 0.8 | 1.0 | 1.9 | 0.099 | 0.3 | 1.57 | 6.6 | 0.094 | 0.1 | 1.91 | 11.3 |
| Example 14 | 0.102 | 2.5 | 0.6 | 4.7 | 0.100 | 0.9 | 0.7 | 6.5 | | | | 100.0 |
| Example 15 | 0.107 | 0.4 | 0.8 | 1.8 | 0.105 | 0.2 | 0.88 | 3.7 | 0.104 | 0.5 | 0.93 | 4.6 |

What is claimed is:

1. A process for preparing microcapsules having a core encapsulated within an inorganic oxide shell, wherein said core comprises at least one active agent and at least one phase changing material, said process comprising:

(a) preparing an oil-in-water emulsion by emulsification of an oily phase comprising at least one active agent, at least one phase changing material and a sol-gel precursor, in an aqueous phase, wherein said aqueous phase comprises at least one inorganic metal salt;

(b) adjusting the pH of the emulsion to be in the range of 3 to 5; and (c) subjecting said emulsion to microcapsule forming conditions; thereby obtaining said microcapsules;

wherein said at least one phase changing material is not liquid at room temperature, and wherein said core has a viscosity of from about 300 cP to about 1,000,000 cP.

2. The process according to claim 1 wherein said at least one active agent is selected from the group consisting of a pharmaceutical agent, a cosmetic agent and a dermatological agent.

3. The process according to claim 1, wherein said at least one active agent is a dermatological agent selected from the group consisting of anti-fungal agents, anti-bacterial agents, anti-inflammatory agents, antipruritic agents, anti-psoriatic agents, anti-acne agents, anti-rosacea agents, and any combinations thereof.

4. The process according to claim 1, wherein said at least one active agent is an anti-acne agent selected from the group consisting of benzoyl peroxide, retinoid, and mixtures thereof.

5. The process according to claim 1, further comprising adding at least one inorganic oxide nanoparticle to said aqueous phase prior, during or after preparation of oil-in-water emulsion of step (a).

6. The process according to claim 1, further comprising adding an inorganic oxide salt to said aqueous phase prior, during or after emulsification of step (a).

7. The process according to claim 1, wherein said oily phase comprises a sol-gel precursor.

8. Microcapsules obtained by the process according to claim 1.

9. The process according to claim 1, wherein said phase changing material is selected from the group consisting of natural or synthetic paraffins, waxes, $C_{10}$-$C_{100}$ alkane, $C_{10}$-$C_{100}$ alkene, $C_{10}$-$C_{100}$ alkyne, aliphatic alcohols, aliphatic fatty acids, and any combination thereof, wherein said aliphatic fatty acid has a molecular formula of $CH_3(CH_2)_nCOOH$, and wherein n=10-100.

* * * * *